United States Patent [19]

Sulc

[11] Patent Number: 4,540,367

[45] Date of Patent: Sep. 10, 1985

[54] DENTAL ATTACHMENT STRUCTURE

[76] Inventor: Josef M. Sulc, 145 Mountain Rd., Wilton, Conn. 06897

[21] Appl. No.: 606,218

[22] Filed: May 2, 1984

[51] Int. Cl.³ .............................................. A61C 13/22
[52] U.S. Cl. .................................................. 433/181
[58] Field of Search ............... 433/172, 173, 180, 181, 433/182, 183, 169, 170, 177

[56] References Cited

U.S. PATENT DOCUMENTS

| | | | |
|---|---|---|---|
| 1,324,476 | 12/1919 | Supplee | 433/181 |
| 1,664,726 | 4/1928 | Adler | 433/177 |
| 2,694,858 | 11/1954 | Cluytens | 433/177 |
| 3,328,879 | 7/1967 | Bax | 32/12 |
| 3,787,975 | 1/1974 | Zuest | 433/170 |
| 3,991,472 | 11/1976 | Lukesch | 433/169 |
| 4,362,509 | 12/1982 | Sulc | 433/181 |
| 4,431,416 | 2/1984 | Niznick | 433/174 |

FOREIGN PATENT DOCUMENTS 1088187 1/1959 Fed. Rep. of Germany .

Primary Examiner—Robert Peshock

Attorney, Agent, or Firm—Pennie & Edmonds

[57] ABSTRACT

A dental attachment structure for a dental appliance, such as a partial denture, an overdenture or bridgework, including female member adapted to be permanently attached to a natural tooth, and a male member having a body of a resilient non-metallic material which supports the appliance. The male and female members are provided with interengaging elements for snap retention of structure. A retention plate secures the female member to a crown or inlay of an abutment tooth. The plate is contoured to provide more securement and a base supporting a socket is angled from the plate toward the edentulous ridge. Securement of members is at a location closer to the center of rotation of the abutment. It is also an aspect of the invention that the male member which supports the appliance may be replaced with a second and subsequent male member with complete accuracy. Replacement of male members will permit the return of the restoration to the original state as problems of wear, retention, or other problems may develop.

11 Claims, 12 Drawing Figures 4,540,367

DENTAL ATTACHMENT STRUCTURE

TECHNICAL FIELD

This invention relates to a dental attachment structure having applicability in the removable attachment and support of any one of a partial denture, an overdenture and bridgework ("an appliance") in an oral cavity. The dental attachment structure includes a pair of cooperating attachment members, one of which is permanently attached to a natural tooth in the oral cavity. The other attachment member comprises a two-part element which is supported by the appliance. This attachment member includes, in part, a plastic component designed to engage with the attachment member supported in the oral cavity and functions to eliminate wear of that attachment member as would otherwise be experienced as a result of repeated attachment of the appliance in the oral cavity over a period of time.

BACKGROUND OF THE INVENTION

Various forms of dental attachment structure for the removable attachment and support of an appliance in the oral cavity are known to the prior art and have been known for quite some time. Typical of a rather early form of appliance is the dental attachment structure illustrated in U.S. Pat. No. 1,324,476 to S. G. Supplee. The Supplee patent, thus, discloses a dental attachment structure that includes a post member and a sleeve member. The post member is designed to be telescopically engaged by the sleeve member. The Supplee patent also discloses a lining received in position in the sleeve member by a cooperating dent and depression. This lining functions in the engagement of members in mounting of a partial denture in the oral cavity, and the engagement of structure is solely through frictional contact between the lining and the post member.

Another representative showing of the prior art is that of U.S. Pat. No. 1,664,726 to H. A. Adler. Without going into detail, it may be stated that Adler describes a dental attachment structure very similar to that described by Supplee. To this end, Adler describes a dental attachment structure including an independent metal leaf spring that provides frictional retention of cooperating members which theretofore were telescoped together. The dental attachment structures described by Supplee and Adler both are considered to suffer from problems of wear of the main components.

Another of the prior art teachings is described in U.S. Pat. No. 3,787,975 to M. Zuest. The Zuest patent discloses a dental attachment structure for removable attachment and support of either partial or full dentures in the oral cavity. The dental attachment structure includes an anchor formed with a socket at the base of a sleeve and a unit for support of the full or partial denture. The anchor is positioned within the root of a tooth that has been endodontically treated. The unit has a structure which is attached to the framework of the full or partial denture and a spherically shaped head which is adapted for removable receipt in the socket.

Still another of the prior art teachings is described in U.S. Pat. No. 3,991,472 to F. Lukesch. The Lukesch patent relates to a denture providing a ball and socket connection between an anchor, and the combination of a plate which supports the prothesis and a pin with a slotted ball-shaped projection which extends from the plate. The pin is threaded at the other end for support in a threaded bore in the plate and the slots provide a spring action for snapping the prothesis into the anchor.

One further representation of the prior art in the field of dental attachment structures is set out in U.S. Pat. No. 4,362,509 which issued to the inventor of the dental attachment structure to be fully discussed below. This patent describes a dental attachment structure which includes a male member permanently mounted either to the partial denture, overdenture or bridgework for receipt in the oral cavity or to a natural tooth within the oral cavity itself. The female member is mounted to the other of the structures. An element of a resilient material is received on and mechanically latched either to the male member or the female member to reside between and in surface-to-surface contact with an extension of the male member and the wall of a pocket in the female member.

The structures described in the patents to Supplee, Adler and Zuest suffer from various problems and disadvantages. The most important disadvantage is the requirement of repair or replacement of the attachment structure in the event that the contact surfaces become worn. Wear of the contact surfaces results from the manner of attachment and support of the appliance within the oral cavity. The Supplee lining is described as formed of metal and most likely a hard metal to provide the characteristic of elasticity or spring required for retention. In use of the appliance over a period of time, and repeated insertion and removal, there will be wearing of the post member which ultimately will require repair or reconstruction of the appliance. The Supplee device is considered to suffer from a further problem, namely a problem that develops from a required shortening of the post member to facilitate mounting to the abutment tooth which may also be short. This shortening of the post member and consequently the sleeve member reduces the area of contact between the lining and the post member resulting in a limited frictional retention.

The problem of wear is considered, also, to manifest itself in the Lukesch structure. In addition, the Lukesch structure is considered to suffer from another disadvantage namely that the slots in the ball-shaped projection result in a weakening in the integrity of the pin. As to the consideration of wear, the routine of inserting and removing the denture several times a day will cause wear along the contacting surfaces of the anchor, and in time, sometimes only in a matter of weeks, these repeated insertions and removal may result in loss of snap retention. And, while there is the capability of replacing the pin with a new pin, it may be difficult to thread a new pin into the plate to extend to exactly the same location as the pin it replaces. Even a small deviation will result in problems with the pin not properly engaging the anchor when the denture is seated.

Wear of contact surfaces is also a problem in the dental attachment structure of Zuest. Zuest, unlike Supplee and Adler, employs no lining or similar structure. Wear of the surface of either or both of the anchor and unit may result and require replacement of the entire component.

The dental attachment structure disclosed in my prior patent addresses the problem of wear of components by adding a replaceable layer of plastic in the form of a sleeve lining or similar structure. The sleeve lining carries mechanical latching elements to interact with a complementary structure, whether it is the female or male member to which it is attached to become a unit, as well as with the other of those members to reside therebetween when the male and female members are mounted together. The mechanical latching elements which unitize the sleeve lining and a member provide a latching force greater than the latching force to maintain the mounted condition of the male and female members. In this manner, the sleeve lining will remain on the appliance when the appliance is removed from the oral cavity.

SUMMARY OF THE INVENTION

The dental attachment structure of this invention can be generally described as including a first member having a retention profile and a base. The retention profile includes a pair of plates which are mounted to a natural abutment tooth either by a crown or following a bonded restoration technique. The base terminates in a cup-shaped structure extending from one plate, an outer plate of the retention profile, which will reside externally of the crown when the first member is mounted by the retention profile. The first member may be characterized as a "female member". The dental attachment structure includes a second member, or male member, which both supports the dental appliance and cooperates with the female member in mounting the dental appliance. The male member may take the form of a cup with a projection extending axially from the base of the cup.

In a preferred embodiment of the invention, the male member is of one-piece construction and formed of a material which displays a measure of resiliency to provide for snap retention of the projection into the cup-shaped structure in mounting the appliance. A plastic, such as nylon or similar material has been found to be sufficiently strong for the use intended, and the resiliency of the material permits snap retention without any requirement, as heretofore in the prior art, of slotting the projection. The material, also, has been found to eliminate problems of wear of the female member. Actually, the male member absorbs all wear as may be incurred by the dental attachment structure over a period of time.

The wall of the cup of the male member is recessed or cutout to accommodate the base of the female member extending from the outer plate of the retention profile. In this manner the male and female members may be telescopically received when mounting the appliance in the oral cavity. In the disposition, the projection of the male member is received in the cup-shaped structure of the female member, while the wall of the cup of the male member surrounds the cup-shaped structure of the female member. A tight interfitting telescopic engagement of members is enhanced by the engagement between the external surface of the cup-shaped structure of the female member and internal surface of the cup of the male member. The recess or cutout in the wall of the cup of the male member will be of a dimension to engage with the extending base.

The female member preferably is formed of metal. In an important aspect of the invention the retention plates are provided with an improved profile which reduces or substantially eliminates weak areas in the crown surrounding the plates. To this end, the inner of the retention plates is contoured to provide a concave surface toward the axis of the abutment tooth. This profile provides a particular advantage where small teeth do not allow for considerable bulk of metal around the retention profile or the dental technician does not contour the crown wide enough to provide for sufficient bulk of metal. In these instances, there may occur breakage of the female member out of the crown in the mouth of the patient. Replacement of the female member is to be avoided since replacement requires an expensive remake of the restoration. Another aspect of the invention, also for the purpose of reducing or substantially eliminating damage to the crown, resides in the design of the female member overall, namely, in the vertical offset of the base and cup-shaped structure in relation to the plates of the retention profile, and particularly the part of the plates of the retention profile to be incorporated within the crown. The offset results in the cup-shaped structure being placed closer to the center of rotation of the abutment tooth. This, in turn, will reduce the leverage effect of chewing forces and improve the odds for preservation of the remaining natural abutment teeth. In addition, by lowering the external base and cup-shaped structure of the female member closer to the edentulous ridge more room will be left for the artificial tooth of the appliance to be placed over it.

In another aspect of the invention, the male member comprises a replaceable component member of the dental attachment structure. To this end, the male member may be removed from and snapped back into a receptacle which may either be a separate part or formed directly within the material of the appliance. This capability assures a simple repeatable replacement without loss of accuracy in the proper alignment between the male and female members. In the prior art, such as represented by the Lukesch patent, it has been found that difficulty is encountered in the replacement of structure, particularly in locating the new structure in the same physical location relative to the other member.

The invention is an improvement over the prior art in that it eliminates the problems of wear of metallic elements that are fitted together, and it is considered the mounting structure provides a superior fit between the members. Other advantages of the invention include rapid and inexpensive replacement of the male member and the immediate restoration of the original retention with perfect fit of the appliance in the oral cavity. These advantages and others will become evident as the description continues.

BEST MODE FOR CARRYING OUT THE INVENTION

Figure 1:
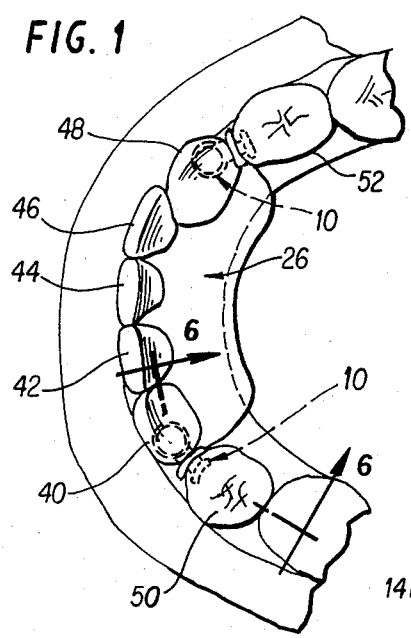
FIG. 1 is a plan view illustrating a portion of the oral cavity and the appliance, located by dental attachment structure, in place therein.

The dental attachment structure 10 comprises an extracoronal connector (hereafter "connector") for use in mounting an appliance in the oral cavity (see FIG. 1). The connector includes two components, including a female member 12 and a male member 14. A support structure 16, illustrated in FIG. 3, for example, serves in one form of the invention as a receptacle for the male member in the base of the appliance. It is contemplated, however, that the male member may be received directly in the base of the appliance thereby to obviate the need of a receptacle.

The female member 12 of the connector remains in the oral cavity permanently mounted on a natural or abutment tooth. A full crown or inlay 18 formed on the tooth supports the female member.

Figure 2:
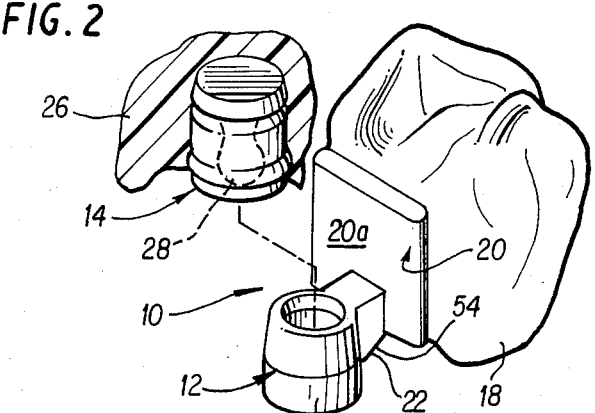
FIG. 2 is a perspective view of the principal components of the dental attachment structure illustrating the manner of mounting.
Figure 5:
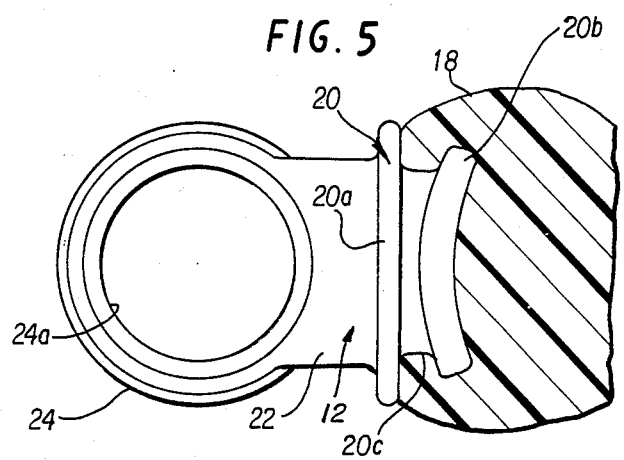
FIG. 5 is a plan view of the other component (the female member) of the dental attachment structure supported by an abutment tooth.

The female member 12, perhaps, may be seen to best advantage in FIGS. 2 and 5. As illustrated, the female member, in elevation, has the general configuration of an L-shaped structure. To this end, the structure comprises a retention plate 20 and a base 22 extending from the retention plate. The base terminates in a cup-socket 24. The retention plate is configured to provide a portion 20a and a portion 20b. With reference to FIG. 5, the portion 20b of the retention plate provides the situs of attachment of the female member to the crown of the natural tooth. As may be seen, the crown substantially surrounds the portion 20b and is received between that portion and portion 20a, within a cut out region 20c. The portion 20a resides in juxtaposition to the outer surface of the crown and supports the female member substantially along the depth of the structure. The portion 20b also acts to compensate for any torque which may develop as the male member 14 and the appliance 26 is removed from the oral cavity.

The base 22 may be of any particular shape and serves the purpose of supporting the socket 24 at a disposition closely spaced from portion 20a of retention plate 20. The socket 24 takes the form of a cup having an upstanding side wall. The outer surface of the side wall of the socket generally is slightly conical in outline and merges with the base 22. The taper is an outward taper in the direction of movement of male member 14. The inner surface of the side wall is contoured to form a necked-down region or constriction 24a. The constriction may be characterized by a convex arc at about the midpoint of the length of the side wall which merges, at its ends, in a concave arc toward the base and entry into the socket.

The female member 12 preferably is formed of a metallic material, such as a metal which conventionally finds use in the field of dentistry. The male member 14 preferably is formed of a plastic material having sufficient strength and durability to permit the repeated connecting and disconnecting movements telescopically of the male and female components in locating the appliance in and removing the appliance from the oral cavity. The material of the male member, also, should provide a measure of resilience to permit a snap retention in mounting the male and female members. In addition, the material of the male member should develop a retaining friction between the male and female members to retain the appliance in a positive manner in the oral cavity, yet permit removal of the appliance from the oral cavity when desired. The male member, accordingly, may be formed of strong nylon, a material that also has been found to eliminate problems of wear of the female member. In this connection, the male member will absorb all wear and as wear increases, the male member is replaceable by a new male member. As will be described, the replacement technique whereby one male member is replaced by another is uncomplex and repeatable, and may be carried out with complete accuracy of alignment between the male member and female member.

The male member 14 of the connector is also characterized by substantially a cup-shaped structure. As such, the male member includes a wall 14a which extends from a base 14b. In addition, a projection 28 extends from the base, along the axis of the wall 14a. The projection has an outer contour which generally is complementary to that of the inner surface of the side wall of socket 24. To this end, the projection includes a constriction at about the midpoint of its length which merges, at its ends, in a convex arc toward the base 14b and the end of the projection. The constrictions allow for a snap fit retention and a mount which will permit a substantial universal movement capability of the appliance. The convex arcs of the projection 28 have equal radii. The concave arcs along the inner surface of the side wall of socket 24 likewise have equal radii, somewhat greater than that of the convex arcs to permit such movement. The male member is completed by a pair of ridges 30, 32 formed on the outer surface of the wall 14a. Each ridge extends completely around the wall, and the ridges are spaced apart so that one ridge is near the base 14b and the other ridge is near the opening between the projection and the inner surface of the wall.

The appliance 26 which may be a partial denture, a bridge or similar dental prothesis may be formed of a dental acrylic. The appliance itself is supported by a male member or a pair of male members which telescopically intercooperate with a female member or a pair of female members in mounting the appliance. This support may be a direct support, illustrated in FIG. 4, or the appliance may be supported by the combination of the receptacle 16 and the male member received in the receptacle, illustrated in FIG. 3.

Figure 3:
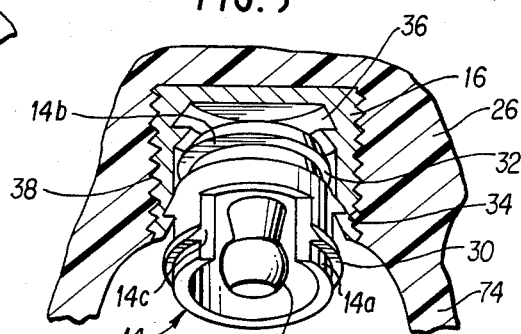
FIG. 3 is a perspective view of one component (the male member) of the dental attachment structure.
Figure 4:
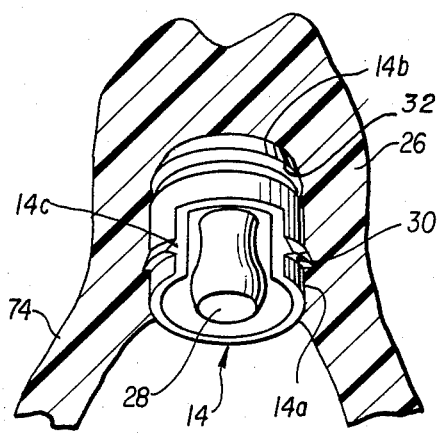
FIG. 4 is a perspective view of the male member illustrating a second manner of mounting the male component to the appliance.

Turning to FIG. 3, the receptacle 16 is illustrated as having a shape like that of male member 14. The receptacle is embedded in the dental acrylic of the appliance. Typically, the receptacle may be embedded in the appliance during the forming process which is carried out according to conventional techniques.

The receptacle 16 provides an internal surface which is complementary to the external surface of wall 14a of male member 14. Thus, a pair of grooves 34, 36 are formed around the internal surface of a wall 16a, and the grooves are spaced to accommodate the ridges 30, 32, respectively. The receptacle may be formed of the same material used for the female member 12, and a serrated outer surface 38 along the wall 16a toward the appliance will maintain the embedded relationship as seen in FIG. 3.

Figure 6:
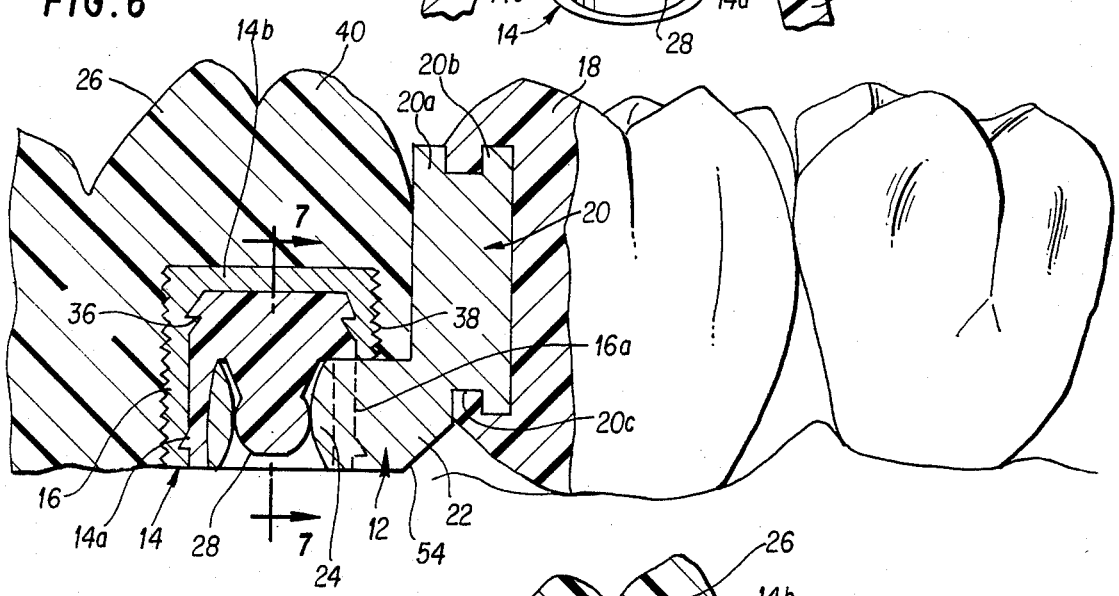
FIG. 6 is a view in section as seen along the line 6—6 in FIG. 1.
Figure 7:
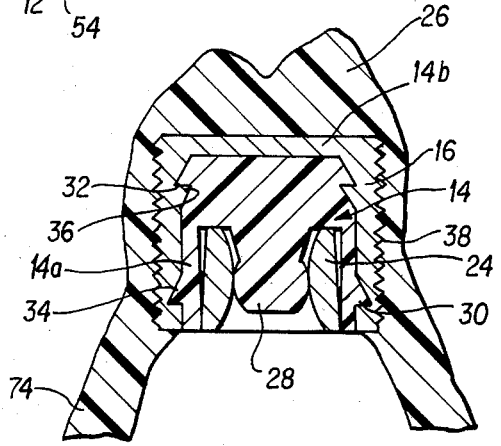
FIG. 7 is a view in section as seen along the line 7—7 in FIG. 6.

FIG. 3 illustrates the male member 14 in a position spaced from a seated position within the receptacle, while FIGS. 6 and 7 illustrate the male member seated within the receptacle and removably secured by the interaction of ridges 30, 32 within grooves 34, 26, respectively. The male member 14, in either form of the invention, that is, in the disposition within the receptacle 16 (FIG. 3) or in the disposition embedded in the dental acrylic of the appliance (FIG. 4) may be removed from the seated position for replacement, or any other purpose. The manner of removal of the male member will be discussed below.

Referring to FIG. 1, the appliance 26 which is illustrated comprises a partial denture formed by a plurality of teeth 40, 42 . . . 48, and a pair of connectors 10 support the partial denture between a pair of abutment teeth 50, 52. Each abutment tooth may be provided with a full crown or inlay 18, as previously discussed.

The appliance 26 may be received into the oral cavity and secured rather easily. To this end, the appliance is moved to position the projection 28 of the male member 14 above the opening into socket 24 of the female member 12. The appliance may be secured in the oral cavity at either a single or a multiple of locations. The end of projection 28 is generally ball-shaped in outline and it moves with a snap fit through the neck-down region 24a as the projection enters into the socket. At the same time the wall 14a of the male member 14 slides along the outer surface of the socket 24 to the fully received position. The friction between the walls and the snap fit of the ball and socket connection provide a positional and positive securement with the aforesaid movement capability, of the appliance in the oral cavity. Both the male member 14 and receptacle 16 are formed with a cutout to accommodate the base 22 within the region of support of socket 24. The cutout 14c in the wall of male member 14 and cutout 16a in the wall of receptacle 16 may be seen in FIGS. 3 and 6.

The female member is considered to provide at least two aspects of improvement over prior art structures. A first of these aspects of improvement resides the staggered alignment of structure, resulting in a vertical offset of the socket 24 in relation to the retention plate 20 incorporated within crown 18. To this end, the base 22 is angled, along a surface 54, toward the edentulous ridge (not shown). A result of the vertical offset is to locate the socket closer to the center of rotation of the abutment tooth. The center of rotation which is not shown resides generally in the region of the root of the abutment tooth, below the edentulous ridge. Since the appliance connection is moved closer to the tooth center of rotation, with a consequent reduction of leverage on the abutment tooth, the odds of preservation of the abutment tooth is greatly improved. In addition, by lowering the socket closer to the edentulous ridge more room will be left for the artificial tooth which must be placed over it. A second aspect of improvement is with regard to the profile of the retention plate 20 incorporated in crown 18 to secure female member 12. Referring to FIGS. 2 and 5, the plate portion 20a is substantially flat and resides against the crown 18; whereas the plate portion 20b is contoured and concave toward the axis of the abutment tooth. In prior constructions, it has been found that retention plates produce weak areas in the casting, particularly with narrow tooth contours. For small teeth the retention plates do not allow for any considerable bulk of metal of the crown to reside around the retention profile. This may be aggravated in circumstances that the dental technician has not contoured the crown sufficiently to provide for sufficient bulk of metal. In these instances the female member may break out of the crown in the oral cavity. Since the female member is not replaceable in the restoration without a complete remaking, there may result a great loss of time, energy and profit to the dentist in corrective action. The retention plate 20 of female member 12 has been found to eliminate or substantially eliminate this problem. Referring still to FIG. 5, it may be appreciated that the concave shape of plate portion 20b provides a significantly greater bulk of metal of crown 18 around the plate portion then would be the case if the plate portion extended toward the closer edge of the crown.

As previously discussed, the male member 14 of connector 10 not only is replaceable, it is replaceable with complete accuracy. Therefore, as problems of wear, retention, and so forth develop, the restoration may be returned to the original state without the large cost usually associated with an entire restoration.

Figure 8:
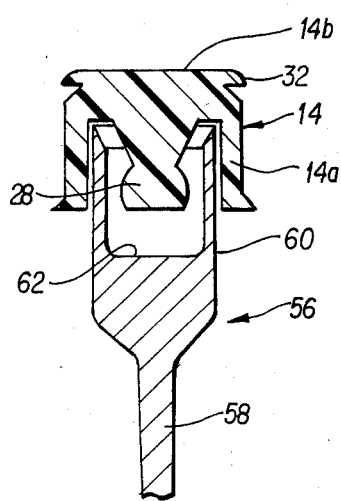
FIG. 8 is a view in elevation of the male member and a tool used in the technique of replacement in the mount of one male member for another.
Figure 9:
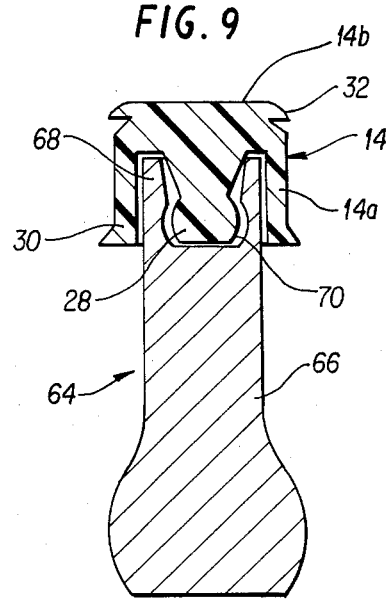
FIG. 9 is a view like FIG. 8 illustrating a tool for seating the male member in the mount.

FIGS. 8 and 9 illustrate a male member 14 to be removed from the acrylic base of the appliance 26 (not shown) and a male member to be replaced in the acrylic base of the appliance, respectively. The male member may be removed and replaced in both forms of the invention wherein the male member is received directly or in combination with a receptacle 16. The one-piece construction of the male member, and the material from which it is fabricated permit these actions, as will be set out. The return of the restoration to the original condition is carried without any destructive action to the acrylic base of the appliance requiring a build up of acrylic material to affix the new component of male member in the existing appliance. As may be apparent, if a build up is required there may be no assurance that the new component will be placed back exactly to the position from which the old component was removed. Even a small deviation will result in problems with the male member not properly engaging the female member when the appliance is seated in the oral cavity.

A cutting tool 56 is provided to remove the male member 14 from the acrylic base of appliance 26 or the receptacle 16. The cutting tool includes a handle 58 and a blade 60. The blade is annular in outline for receipt between projection 28 and the inner surface of wall 14a of the male member. The cutting tool, in essence, cores out the projection and that portion of base 14b which supports the projection. A stop 62 in the form of a surface interacts with the end of the projection to limit movement of the cutting tool in travel toward the acrylic base only to the plane of the outer surface of base 14b. When the projection and portion of the supporting base is cored out it may be easily removed. The hollow ring which remains, then, may be collapsed inward and removed. A seating tool 64 serves in mounting a new male member 14 in the location vacated by the male member which is replaced. To this end, the seating tool includes a handle 66, a prong 68 in the form either of a plurality of fingers with a cylindrical tip or a totally cylindrical finger, or the equivalent, and a base 70 which interacts with projection 28. The base and finger (or tip) act to snap the male member into place. The male member will be physically restrained by interaction of ridges 30, 32 in grooves 34, 36, respectively.

Figure 10:
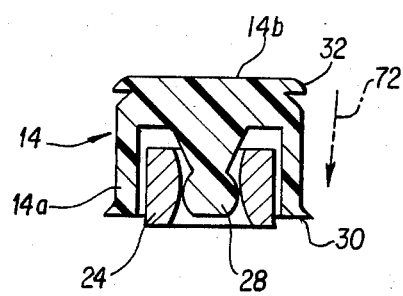
FIG. 10 is a schematic view of a portion of the component parts of FIG. 6.
Figure 11:
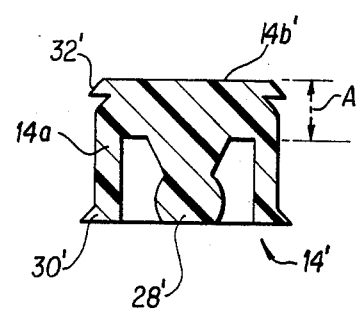
FIGS. 11 and 12 are views of the male member and a fabricating component, respectively.
Figure 12:
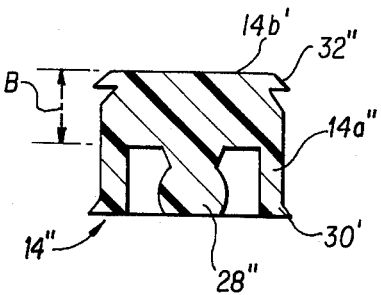

Bonded restoration techniques for use with connectors for removable appliances eliminate the need for placing a full crown over an abutment tooth. Instead, a relatively small metal flange is fabricated. The surfaces of the abutment tooth and the metal flange that will come in contact are etched with acid solution to provide microscopic undercut areas on the tooth surface and on the metal for bonding of the metal flange to the selected surface(s) of the tooth. Thus, a missing tooth may be replaced by etching the adjacent teeth in the areas where flanges carrying the replacement tooth will be bonded. This technique now is very popular because it is more conservative than conventional crowns (much less of the natural tooth structure is removed) and less costly. The success of this type of restoration; however, depends to a great measure on the ability of the metal flange to remain securely bonded to the abutment tooth, and not to become dislodged by forces as may be developed during the chewing cycle. The connector of the invention provides an ideal construction since the male member of nylon provides a cushioned flexible connection that will protect the bond and assist in prevention of the female member from breaking away from the abutment tooth. The overall concept in the connector of the invention, in addition to the resiliency and flexibility of the male member, includes the provision of a small space between the male and female members to allow for up and down movement of the members as well as hinge action between the members. Turning to FIG. 10, there is illustrated a portion of socket 24 of female member 12 and the male member 14. The projection in a quiescent or nonchewing condition, extends just beyond the neck 24a to provide a space between the lower surface of base 14b and the upper surface of the socket. The space allows for movement of the male member which supports the appliance in the direction of arrow 72 beyond a full snap position of receipt of the male member into the socket. A limiting factor in the vertical movement of the appliance is how much the tissue (gums) may compress. When the appliance is seated in the oral cavity the saddle 74 (see FIG. 3, for example) of the appliance comes into full contact with the gums just as the projection of the male member snaps over the neck 24a of the socket of the female member. Then, under additional load on the appliance, during chewing, the appliance can settle and recoil back as the tissue resiliency will allow. In this manner, the forces that are generated during the chewing cycle are distributed over the entire edentulous ridge area that supports the appliance. If the fit between the male and female members of the connector 10 was a totally rigid snap fit the appliance could not move any further down into a heavier contact with the tissue. Consequently, all the extra force would have to be absorbed by the abutment tooth. The space, however, in a quiescent or passive position (the appliance is fully seated and the male member just engages below the neck in the snap fit in the female member, but there is no extra load on the appliance and no compression of the tissue) will accommodate movement. The dimension of the space will equal the maximum possible additional downward movement that the appliance may undergo. The invention provides a unique way of creating the space as well as the receptacle for placement of the male in the acrylic base material. Reference now may be directed to FIGS. 11 and 12. FIG. 11 illustrates a male member 14 which is a replacement component and FIG. 12 illustrates a male member 14" which is a fabricating component. The difference between the two male members resides in the thickness of each base 14b' and 14b", and consequently the length of the projections 28' and 28" respectively. Male member 14' has a base having a thickness "A", while fabricating male member 14" has a base of somewhat greater thickness "B". In the appliance fabrication process, the fabricating male member is used in a following manner. The completed bridge carrying the female member is placed on a plaster working model of the mouth of the patient. The bridge rests on this model in exactly the same position as it will be in the oral cavity. The model includes a duplication of the ridge areas on which the appliance will rest. The fabricating male member is snapped into the socket of the female member. The fabricating male member fits tightly and does not allow any movement. The inside upper surface of the fabricating male member rests directly on the top surface of the socket of the female member as the projection snaps fully over the neck 24a inside the socket. The fit is a snug fit. There is no space to allow for any movement. The appliance which may be a partial denture is now formed on the model of the mouth. The acrylic base material will flow and harden around the outside of the fabricating male member and over the duplication of the jaw. Artificial teeth are set into the hardening acrylic. After the acrylic completely cures, the partial denture is removed from the model. This technique is the technique carried out in the form of the invention which does not utilize the receptacle 16. The process is continued by coring out the center portion of the fabricating male member, collapsing the remaining walls inward, any small pointed instrument may be used, disengaging the undercut ridges, and then pulling the remaining part of the fabricating male member out of the acrylic. An exact duplication of the outside shape of the fabricating male member including the grooves 34, 36 will remain in the hardened acrylic. The male member now may be seated by the seating tool and snapped into the acrylic base and socket created by the fabricating male member. A free space, however, will remain between the top surface of the socket of the female member and the inside upper surface of the male member. The space will equal the difference between the dimensions "A" and "B".

The space accommodates the additional force (biting, chewing) the appliance may undergo to move further down compressing the tissue under the acrylic saddle and distributing the load over the large area of the jaw. If there was no space between the inside top surface of the male member and the top surface of the socket of the female member, the appliance would resist this movement under load and the force effect would be localized in the female member and the abutment tooth over the larger area of the jaw ridge. While the so-called "resilient" concept is known, the manner of fabricating and locating the male and female members of the connector, both initially and in the replacement of a member, whereby there is instant repeatability is a great improvement over existing techniques.

In summary, the connector and its make-up provides unequal protection of the male and female members, permits a drastic reduction both in cost of manufacture and in adapting the appliance to the oral cavity, and it serves in providing overall comfort of wear.

I claim:

1. Dental structure for the removable mounting of a dental appliance, such as a partial denture, bridge or similar dental appliance in an oral cavity comprising:
   (a) a female member comprised of a metallic material;
   (b) mounting means on said female member adapted for mounting the same permanently on an abutment tooth within said oral cavity; said mounting means formed by at least one plate of concave curvature toward the axis of said abutment tooth;

(c) a male member comprised of a resilient non-metallic material;
(d) support means for removably supporting said male member within an opening in the base portion of said dental appliance; and
(e) means carried by said male and female members for releasable engagement of said members by snap fit engagement within said oral cavity.

2. The dental structure of claim 1 wherein said male member has the form of a cup-shaped body including a base and a wall surrounding an opening into said body, and wherein said support means includes at least one ring which circumscribes the outer surface of said wall of said body, each said ring adapted for releasable latched receipt in a groove in said opening.

3. The dental structure of claim 2 wherein said support means includes a pair of rings, one ring being located adjacent the opening into said body and the other ring being located adjacent the base of said body, and a pair of grooves in said opening into which said rings are received and releasably latched.

4. The dental structure of claim 2 wherein said male member includes a projection extending from the base toward the opening of said cup-shaped body, and wherein said female member includes a socket into which said projection is received when said male and female members are releasably engaged.

5. The dental structure of claim 1 wherein said female member includes a socket, and a base, said base being supported by said mounting means and, in turn, supporting said socket in a disposition spaced from said mounting means.

6. The dental structure of claim 5 wherein said mounting means includes a second plate spaced from said concave plate, and wherein said base is supported by said second plate.

7. The dental structure of claim 5 wherein said base is angled from said mounting means toward the endentulous ridge in said oral cavity thereby to locate said socket and said location of releasable engagement of said male and female members vertically closer to the center of rotation of said abutment tooth.

8. The dental structure of claim 5 wherein said male member has a cup-shaped body including a base and a wall, and said wall having a cut-out region to accommodate said base of said female member when said male and female members are releasably engaged.

9. The dental structure of claim 6 wherein said concave plate is contoured to approximate the shape of said abutment tooth, and said concave plate adapted to be substantially enclosed within a crown or inlay of said abutment tooth, while said second plate is juxtaposed to said crown or inlay.

10. The dental structure of claim 1 wherein said support means comprises a receptacle having a base and a wall terminating at an opening into said receptacle, said receptacle adapted for permanent mounting on said appliance and means on both said male member and receptacle for releasably latching said male member to said receptacle.

11. The dental structure of claim 10 wherein said male member has the form of a cup-shaped body including a base and a wall, and said releasable latching means includes at least one ring which circumscribes the outer surface of said wall of said body and a like number of grooves in the inner surface of said wall of said receptacle for receipt of said rings.

* * * * *